(12) United States Patent
Harding et al.

(10) Patent No.: US 7,044,936 B2
(45) Date of Patent: May 16, 2006

(54) CATHETER CONNECTOR WITH PIVOT LEVER SPRING LATCH

(75) Inventors: Richard Harding, Reinholds, PA (US); Jeffrey Vitullo, Pottstown, PA (US)

(73) Assignee: Arrow International Inc., Reading, PA (US)

( * ) Notice: Subject to any disclaimer, the term of this patent is extended or adjusted under 35 U.S.C. 154(b) by 463 days.

(21) Appl. No.: 10/225,782

(22) Filed: Aug. 21, 2002

(65) Prior Publication Data
US 2004/0039373 A1   Feb. 26, 2004

(51) Int. Cl.
A61M 5/178 (2006.01)
A61M 25/00 (2006.01)
A61M 5/00 (2006.01)

(52) U.S. Cl. .............. 604/167.03; 604/165.02; 604/246; 604/167.01; 604/523

(58) Field of Classification Search .......... 604/167.03, 604/167.01, 165.02, 246–250, 523, 167.02, 604/165.01
See application file for complete search history.

(56) References Cited

U.S. PATENT DOCUMENTS

| 4,015,336 | A | * | 4/1977 | Johnson ................... 433/95 |
| 4,187,848 | A | | 2/1980 | Taylor |
| 4,838,873 | A | * | 6/1989 | Landskron et al. ........ 604/533 |
| 4,842,592 | A | | 6/1989 | Caggiani et al. |
| 4,929,243 | A | | 5/1990 | Koch et al. |
| 4,973,312 | A | | 11/1990 | Andrew |
| 5,460,615 | A | * | 10/1995 | Storz ..................... 604/167.03 |
| 5,464,400 | A | | 11/1995 | Collins |
| 5,542,933 | A | * | 8/1996 | Marks ..................... 604/188 |
| 5,725,504 | A | | 3/1998 | Collins |
| 5,921,968 | A | * | 7/1999 | Lampropoulos et al. .... 604/246 |
| 5,931,671 | A | | 8/1999 | Hoffman |
| 5,989,240 | A | | 11/1999 | Strowe |
| 5,992,899 | A | | 11/1999 | Strowe |
| 6,017,356 | A | * | 1/2000 | Frederick et al. .......... 606/185 |
| 6,050,976 | A | | 4/2000 | Thorne et al. |
| 6,096,024 | A | | 8/2000 | Graves et al. |
| 6,228,059 | B1 | | 5/2001 | Astarita |
| 6,245,044 | B1 | | 6/2001 | Daw et al. |
| 6,254,589 | B1 | | 7/2001 | Raoz |
| 6,260,890 | B1 | | 7/2001 | Mason |
| 6,328,713 | B1 | | 12/2001 | Hollister |
| 6,458,103 | B1 | * | 10/2002 | Albert et al. ............ 604/167.03 |
| 6,572,590 | B1 | * | 6/2003 | Stevens et al. ............ 604/246 |

\* cited by examiner

Primary Examiner—Sharon Kennedy
(74) Attorney, Agent, or Firm—Amster, Rothstein & Ebenstein LLP

(57) ABSTRACT

A catheter connector for coupling to a catheter, the connector having a body part, a tubular shaped compressible plug situated in a bore in part, with the proximal end of the catheter insertable into the bore of the plug, and a lever pivotably mounted to the housing part. Pivoting of the lever applies an axial force on one end of the plug causing the plug to deform radially inward and tightly engage the proximal end of the catheter.

19 Claims, 7 Drawing Sheets

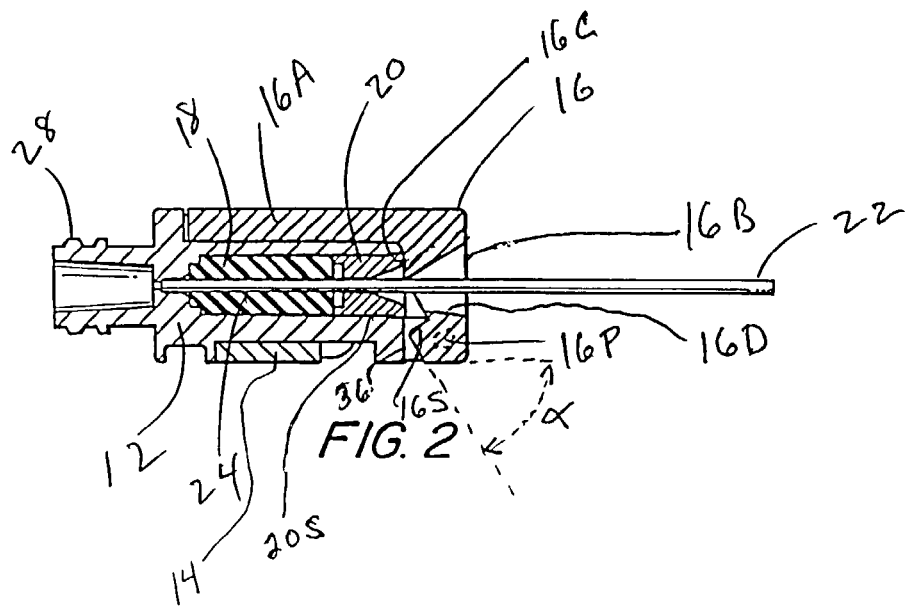
FIG. 2
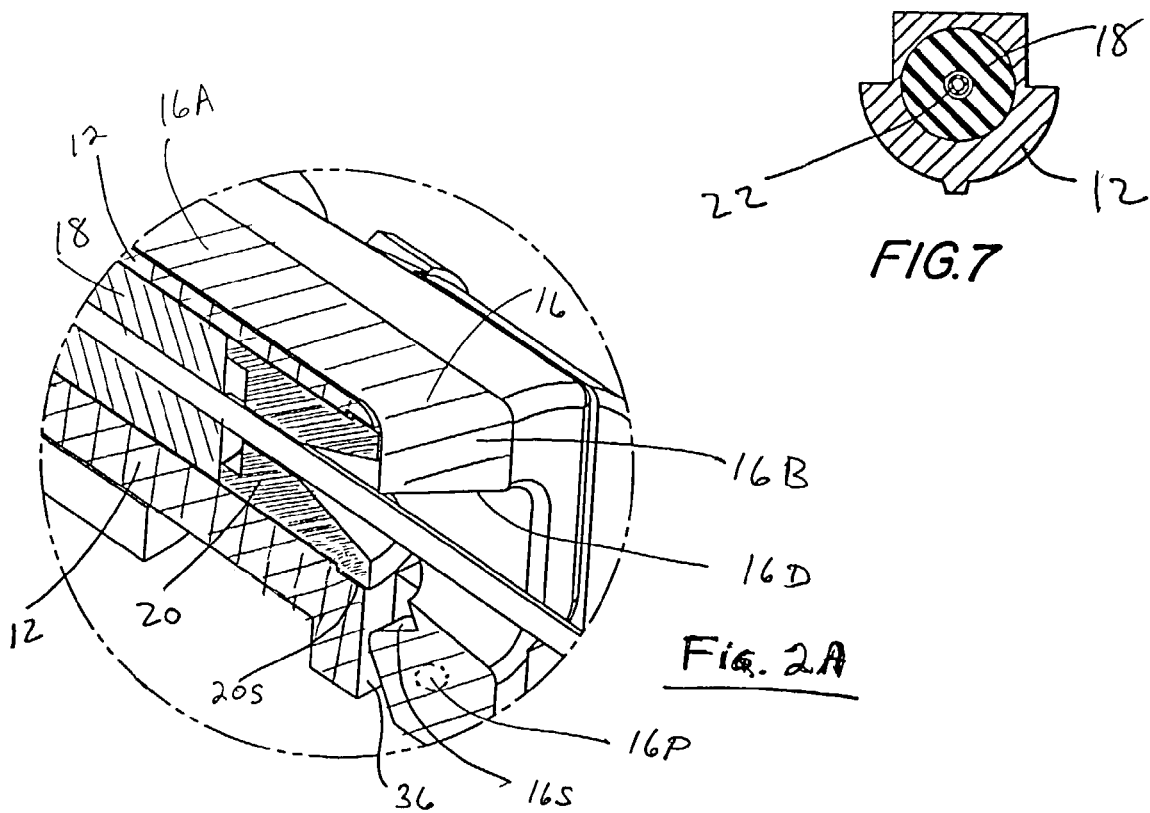
FIG. 7
Fig. 2A

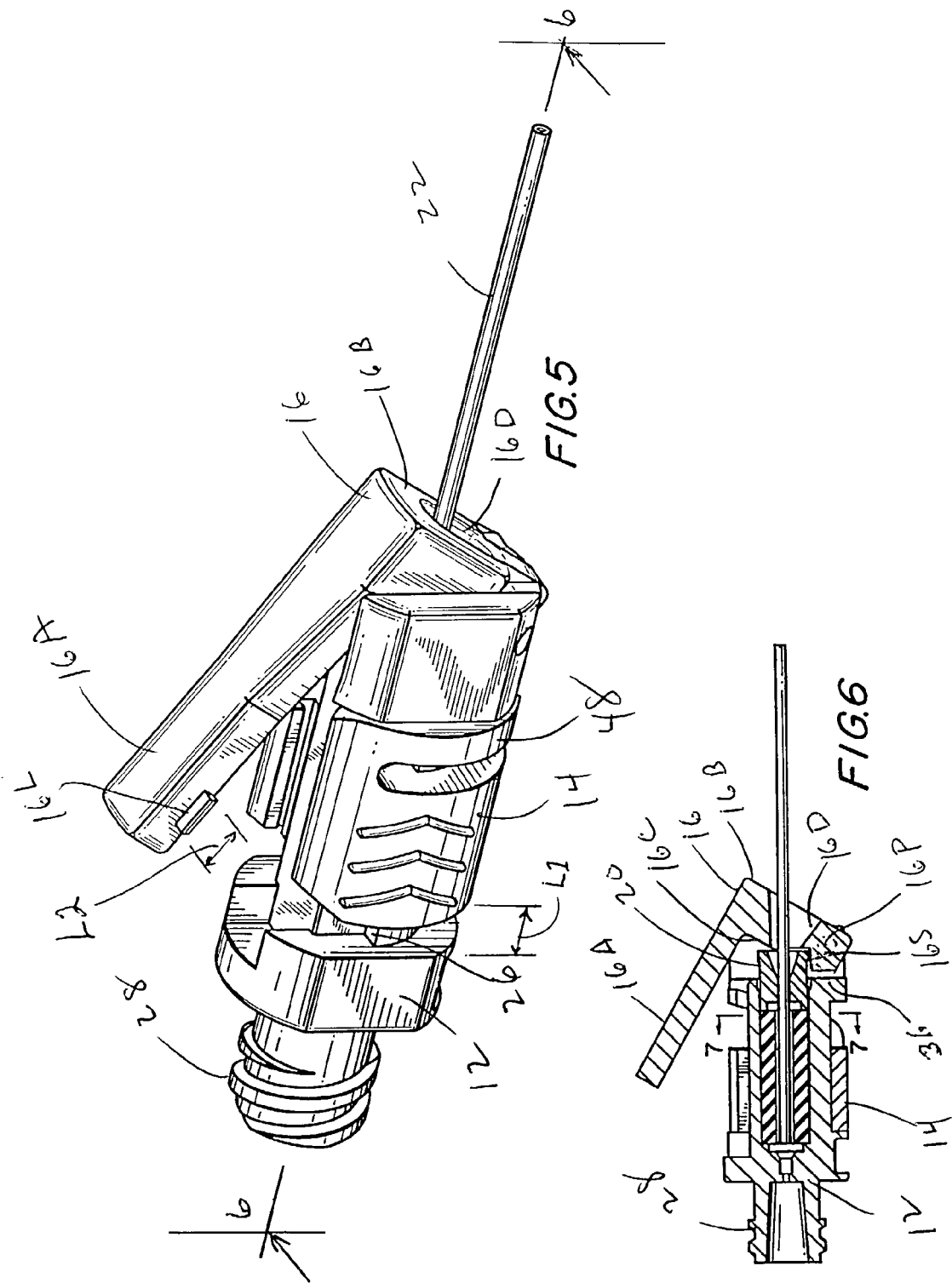

CATHETER CONNECTOR WITH PIVOT LEVER SPRING LATCH

BACKGROUND OF THE INVENTION

This invention is in the field of catheter connectors wherein a catheter connector is coupled to the proximal end of a catheter.

Many catheters, including but not limited to epidural catheters, need to be coupled to catheter connectors situated near the insertion site on a patient. Such a connector secures the proximal end of a catheter from both axial and transverse movement, and often includes one or more fluid couplings for communicating fluids into or out of the catheter.

It is important for the surgeon and other medical personnel to be able to make this coupling of the connector with the proximal end of the catheter quickly, easily and securely. Also it is desirable for the connector to be relatively inexpensive, if possible, since these are often disposable, non-reusable devices which adds to the already expensive cost of invasive medical procedures.

The objects of coupling securely, quickly, easily and economically often call for design features that are in conflict with each other. With regard to a secure coupling that bars axial or transverse movement of the catheter, prior art devices usually apply inward radial compression to one or more outer surface areas of the catheter; however, excessive pressure will collapse the soft tubular catheter and at least partially close the inner fluid passageway, and insufficient pressure will not hold the catheter securely.

This coupling is necessarily a manual event by the user's hands and fingers. Thus, even if the user were able to apply the ideal amount of compressive force on a catheter on one occurrence, such would not necessarily happen on the next occurrence. It is most difficult for users of these devices to always select the correct gripping force in the many various medical procedure circumstances and in the extremely limited time to make the decision.

In addition to the above-described objective of securely engaging the catheter, the coupling procedure needs to be easy and quick. There is little time for a doctor or nurse to adjust and/or study the device.

Numerous prior art devices apply inward radial force on the catheter by simply pressing inward with a rigid element of the connector. Such force is applied to one specific outer area, or is applied circumferentially around the catheter outer wall by a compressible collar surrounding the catheter. In the latter case the compressible collar is situated coaxially within the bores of a pair of mating sleeves which are threadedly engaged. When these sleeves are screwed together, they apply axial force to the collar that is then deformed radially inward against the catheter. Such rotation of one sleeve relative to another necessitates use of two hands by the operator. Such two-handed operation requires time and coordination, and as discussed above, the user is unlikely to be able to apply the same force every time. Of the many prior art catheter connector devices which use threaded elements to achieve deformation of a plug through which a catheter extends, U.S. Pat. No. 5,464,400 to Collins illustrates male and female coupling elements which axially compress a hexagonal slug. As with other threaded couplings, two hands are required; there is no contemplation of operating this device with one hand or of designing any device for such operation.

Another typical prior art connector structure having telescoping sleeves threaded for rotation by a two-handed operation that compresses a collar 15 is seen in U.S. Pat. No. 6,260,890 to Mason.

U.S. Pat. No. 6,228,059 to Hoffman shows a still different locking means, for a trocar, where a locking element 58, as seen in FIGS. 2 and 3, bears down at one area on the side wall of instrument 34. U.S. Pat. No. 6,096,024 to Graves et al. shows a pivoting latch which engages the side wall of a needle cannula. U.S. Pat. No. 5,931,671 to Hoffman discloses a pair of compression elements that move transversely inward to releasably engage and hold a central tube.

This long-practiced concept of applying lateral force directly to a central tube or element is seen most clearly in U.S. Pat. No. 5,725,504 to Collins, where a simple cam lever 28 pivots to engage and deflect wall 27 against hub 12.

The prior art devices described above demonstrate that the long-established modes to secure a central shaft, whether it is a rigid or soft tube or shaft, are either: (a) to use a pivot lever to apply an inward radial force directly onto the side wall of the central shaft, or (b) to use a pair of threaded sleeves, rotatable by a two-handed operation, to apply an axial force to a collar which in turn applies an inward radial force to a central tube.

The more extensive use of catheters and the more intricate surgical procedures has led applicants to an approach which utilizes some known elements and combines them in a new and most useful way. The present invention seeks to overcome all of the above-described faults and disadvantages in prior art catheter connectors with a new device that allows coupling to be secure, quick, easy, uniformly applied and achievable with a single hand.

SUMMARY OF THE INVENTION

The new catheter connector uses a pivoting lever to create and apply an axial force to an elastically deformable collar or plug which is enclosed on its outer circumferential and opposite end surfaces, and can deform radially inward. Furthermore, this inward force is generally uniform all the way around the catheter's outer surface, which reduces the possibility of an extreme localized force that would collapse the catheter. A still further benefit is that the axial compression is affected along the length of the plug and then radially inward, which distributes the force over a very wide surface area of the catheter. This creates a very large frictional force to capture and hold the catheter from any axial or transverse movement with minimal danger of collapse.

Also, the lever action allows the user, with a quick simple motion, to make the coupling and to apply the same correct force to the catheter every time. This is possible since the lever moves through the same arc, and its shoulder moves the same axial distance every time.

Also, this device can easily be operated to open or close with a single hand, by flipping a finger or thumb.

A second embodiment of the invention disclosed herein utilizes a collar or plug with flats on the outer surface. In cross-section such a plug could be, for example, hexagonal or octagonal, where the maximum outer diameter would be between two opposite points and the minimum outer diameter would be between two opposite sides or flats. An alternative could be essentially round outer diameter with intermittent flats, where the maximum outer diameter would be between two opposite outer circular arc segments and the minimum outer diameter would be between two opposite sides or flats. Such a plug is situated generally snugly within a circular bore of a sleeve such that when axial force is applied to such plug, it deforms radially outward in the areas of the flats; however, the bore walls bar the plug from further outward deformation, and thus further axial force causes the plug to deform radially inward against the catheter.

In both of the above-described embodiments the application of axial force to the tubular plug is achieved by a lever pivotally mounted on the connector housing. Such lever pivots about an axis perpendicular to the central longitudinal axis of the catheter and of the connector, and a shoulder of the lever applies the axial force to the plug or to a plunger or annular pressure element contacting the end of the plug. Such lever can easily be pivoted by a user's thumb while he grips and holds the connector body with his palm and fingers.

This axially compressed plug resiliently urges the lever to return to its open position, but a latch is provided to hold the lever in its pivoted and closed position, until released. The latch is established by projections on the lever and mating recesses in the connecting body, or vice versa. In a preferred embodiment a portion of the body which includes the recesses is axially slidable against a spring element thereon, to effect release of the lever. This manual step can also be done by one hand of the user. Upon release, the lever pivots to its open position because of the compressed plug in contact with the lever, and the catheter is then released.

This disclosure herein shows two preferred embodiments of lever and connector body construction, with the understanding that numerous variations are possible.

BRIEF DESCRIPTION OF THE DRAWINGS

FIG. 2 is a longitudinal sectional view taken along line 2—2 in FIG. 1, FIG. 2A is an enlarged fragmentary sectional view of a portion of FIG. 2, FIG. 3 is a transverse sectional view taken along line 3—3 in FIG. 1, FIG. 5 is a top front perspective view of the new catheter connector of FIG. 1 with the lever in open position, FIG. 6 is a longitudinal sectional view taken along line 6—6 in FIG. 5, FIG. 7 is a partial transverse sectional view taken along line 7—7 in FIG. 1.

DETAILED DESCRIPTION OF THE PREFERRED EMBODIMENTS

Figure 1:
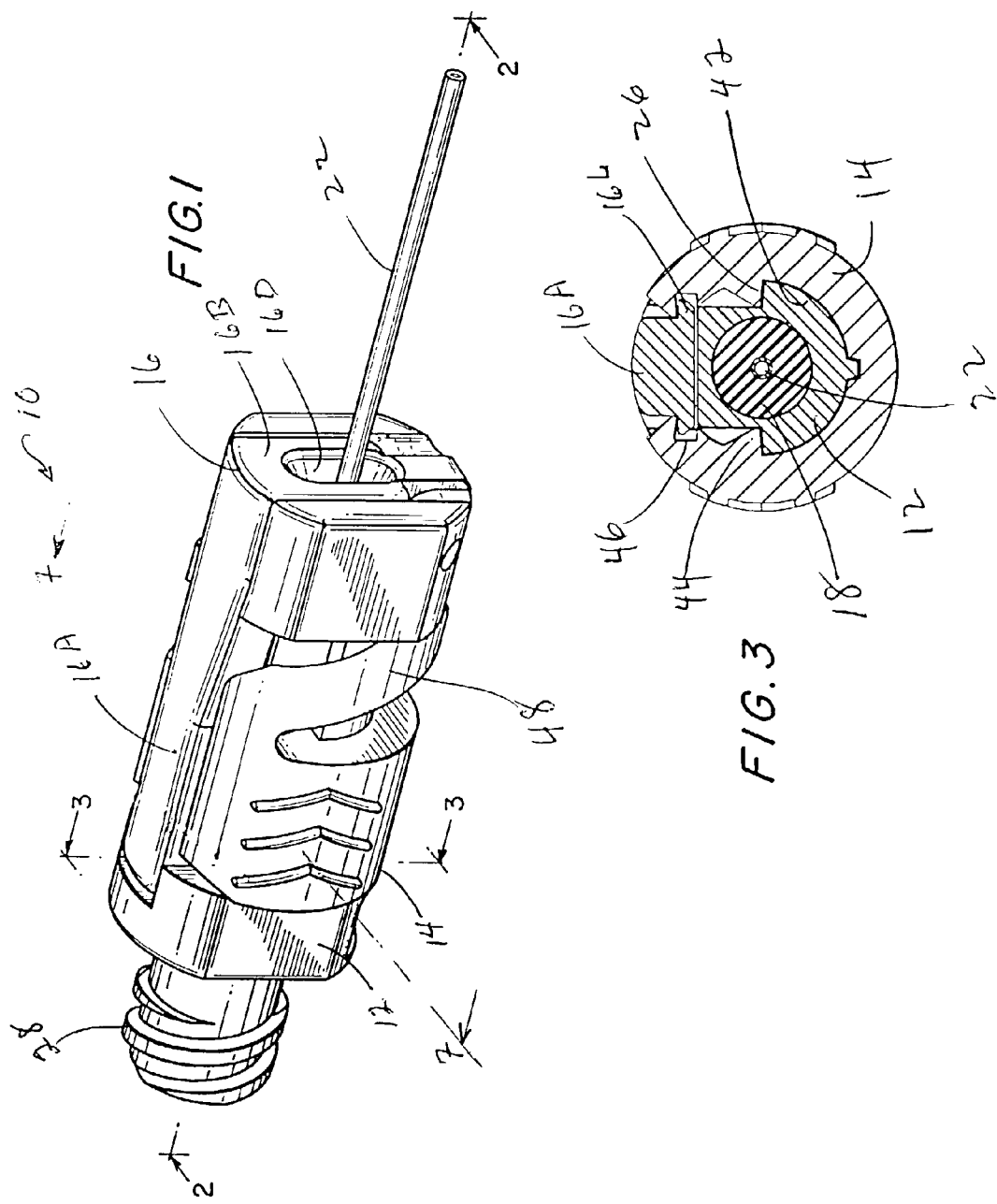
FIG. 1 is a top front perspective view of the new catheter connector with its lever in closed position.
Figure 4:
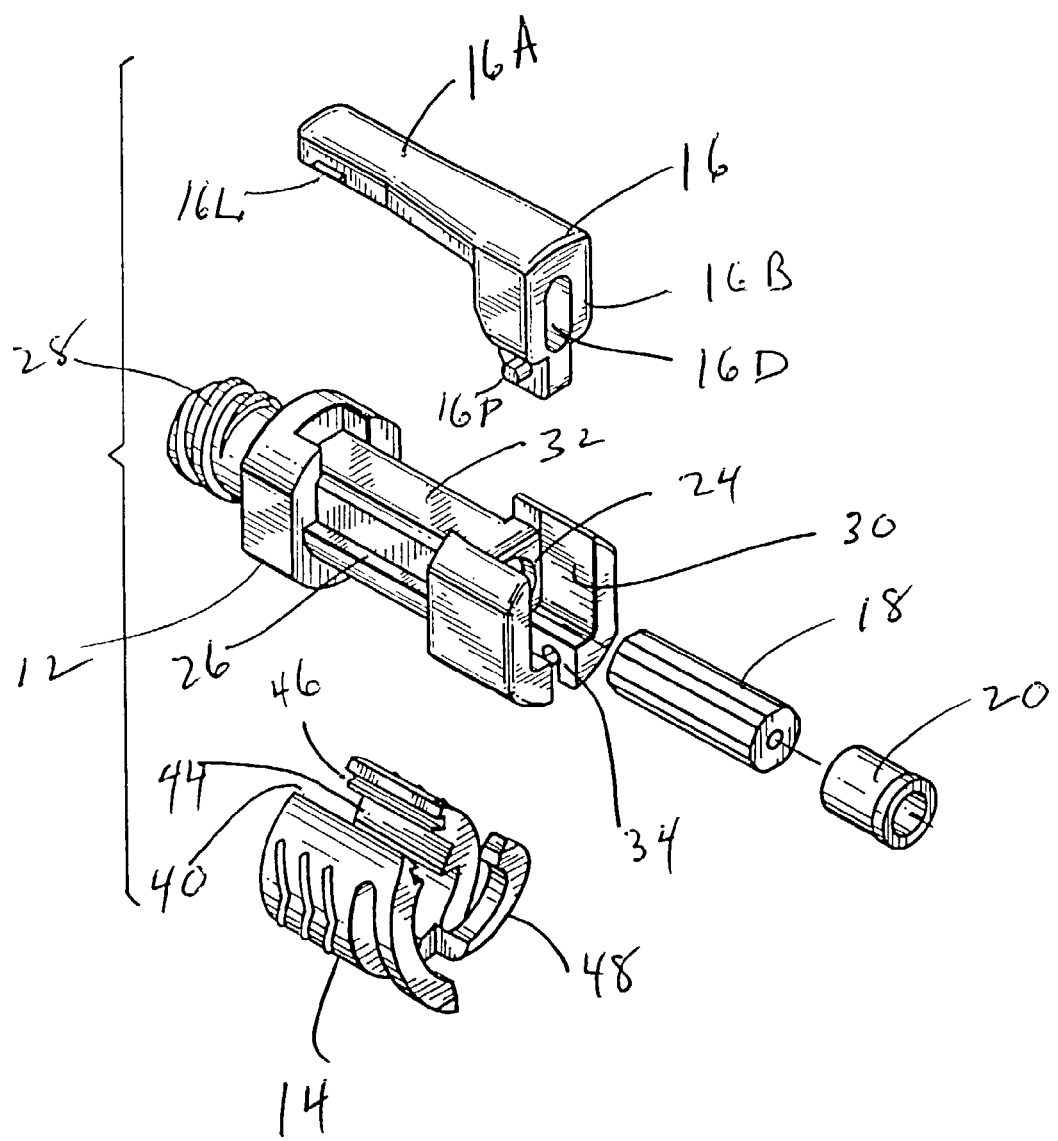
FIG. 4 is an exploded perspective view of the connector of FIG. 1.
Figure 8:
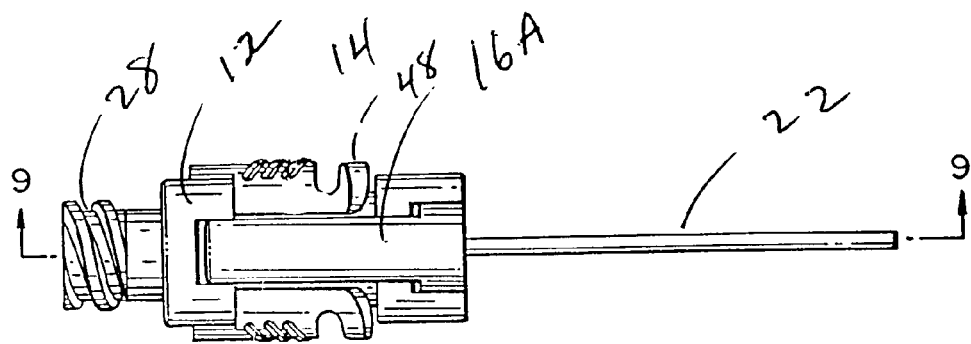
FIG. 8 is a top plan view of a second embodiment of the new catheter connector with the spring latch and the lever in closed position.
Figure 9:
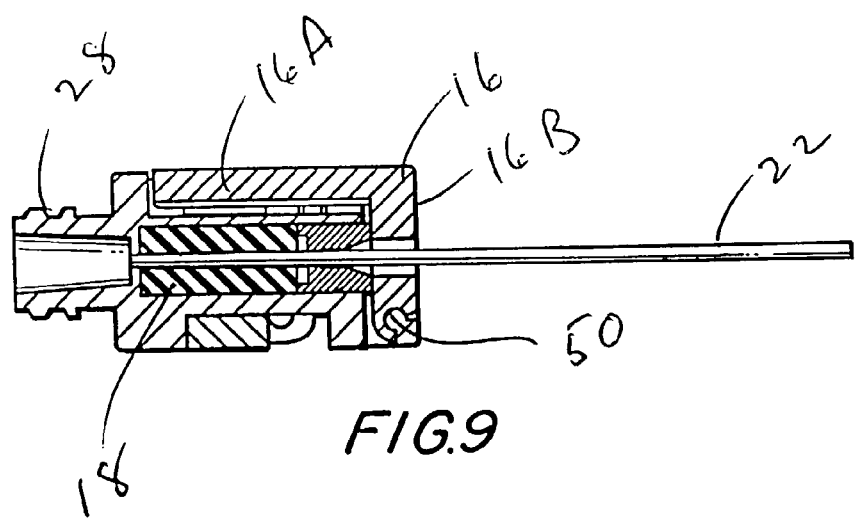
FIG. 9 is a longitudinal sectional view taken along lines 9—9 in FIG. 8.
Figure 10:
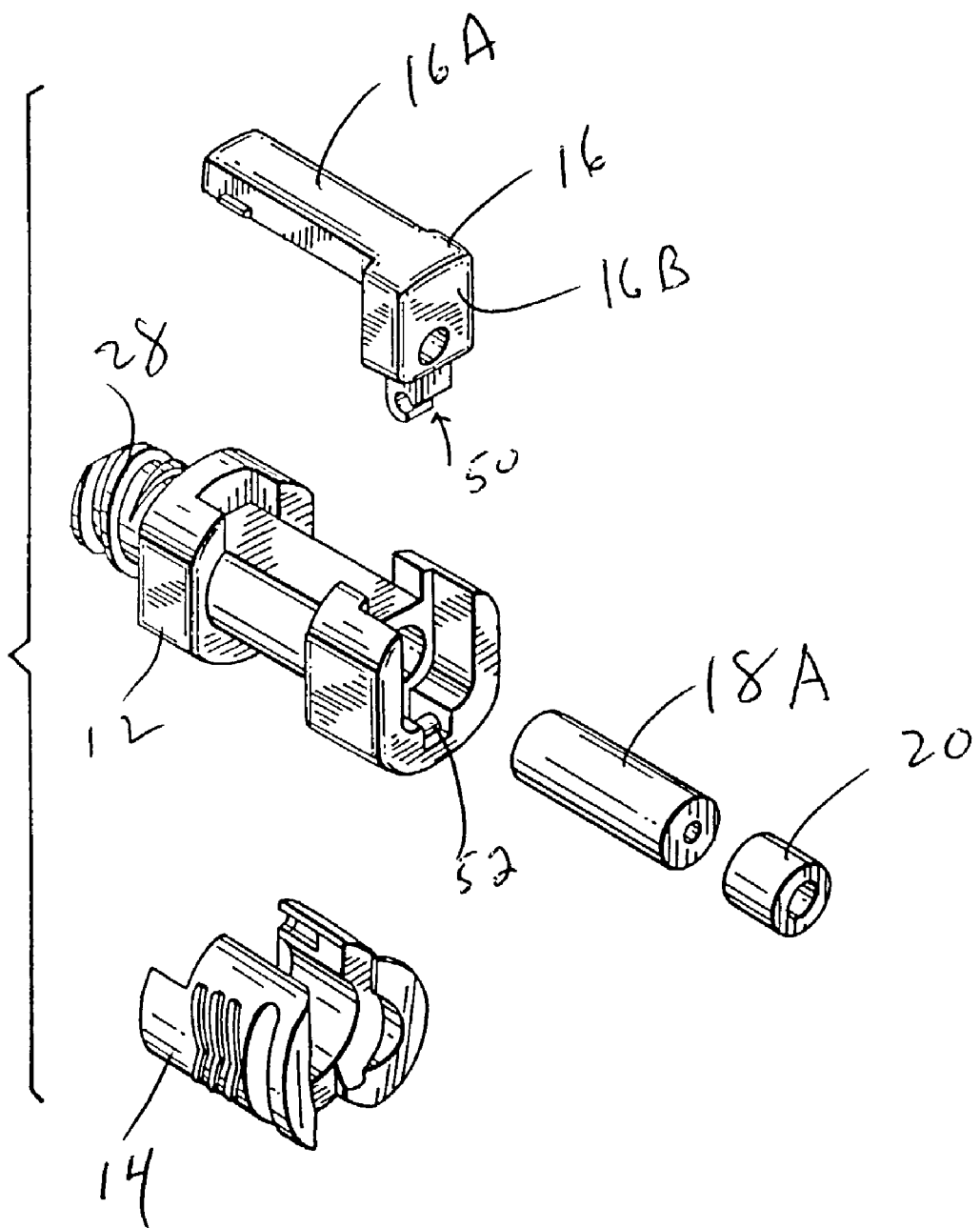
FIG. 10 is an exploded perspective view of the connector of FIG. 8.
Figure 11:
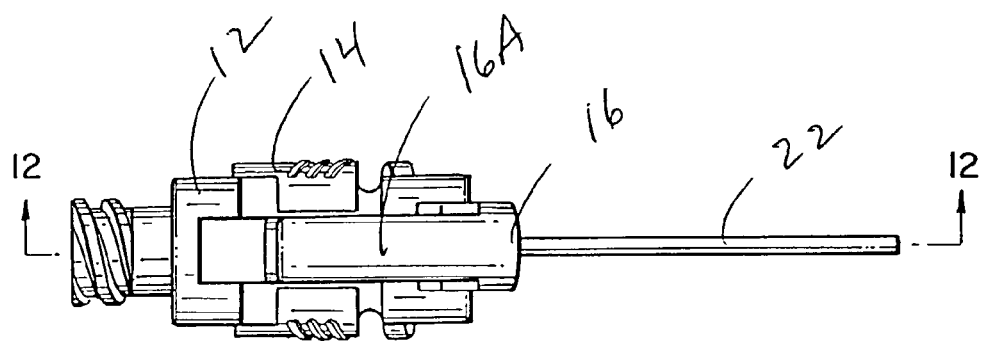
FIG. 11 is a top plan view of the connector of FIG. 8 with the spring latch and lever in open position.

FIGS. 1–7 illustrate a first embodiment 10 of the new catheter connector, which has open and closed positions, as will be explained below. The principal components as best seen in FIGS. 1 and 4 are the connector body 12, spring latch 14, pivot lever 16 with its arm 16A and lever body 16B, compressible elastically deformable plug 18 and plunger 20. FIG. 10 shows another embodiment 18A of the compressible plug, the latter being circular in cross-section. Plugs having hexagonal, octagonal and other cross-sections are interchangeable. FIG. 1 also shows catheter 22 coupled to connector 10.

As further seen in FIGS. 1–7 and particularly in FIG. 4, the body 12 is an elongated member having a central bore 24, a first longitudinal ledge 26, threaded proximal end 28, recess 30 to receive the lever body 16B, recess 32 to receive the lever arm 16A, and recess 34 to receive the lever pivot pin 16P. FIG. 2 further shows lever shoulder 16S at angle ∝ of 45° that abuts stop 20S of connector body 12.

A general description of the operation of this device, which will be later described in detail, is as follows. Beginning with open position seen in FIGS. 4, 5 and 6, the proximal end of catheter 22 is inserted through rigid plunger 20 into the bore of compressible plug 18 which is already situated in bore 24 of body 12. Next, lever arm 16A of lever 16 is pivoted counterclockwise until (as seen in FIG. 2) its compression edge 16C applies an axial force to the left, onto rigid plunger 20, which applies such axial force onto the end of compressible plug 18. This plug is generally confined in bore 24 of body 12 and then deforms radially inwardly against the outer circumferential body of catheter 22. To be described later latch spring means retains this lever in its closed position until released.

As seen in FIGS. 1–6 and 2A, the lever 16 has its pivot pin 16P engaged in body recess 34 (see FIG. 4), its body 16B in body recess 30 and its arm 16A in recess 32. This lever arm 16A is pivotable clockwise to its open position seen in FIGS. 2A, 5 and 6, where the lever shoulder 16S abuts bottom surface 20S of plunger 20 which limits the lever from pivoting beyond the 45° angle shown.

The next principal element is compressible plug 18 made of foam rubber or comparable material. This plug is a tubular member having a bore diameter adapted to easily receive catheter 22 and an outer diameter adapted to easily fit into bore 24 of body 12. This plug has length such that when its proximal end abuts the proximal end of bore 24, its distal end will engage plunger 20. Since plug 18 is confined by bore side and end wall surfaces, an axial force of plunger 20 applied to the distal end of plug 18 will compress and cause it to deform radially inward against the proximal end of catheter 22.

The deformed plug will apply radial inward force along the length of the plug around the circumference of catheter 22, thus snugly capturing it from axial or transverse movement. The forces applied will securely engage the catheter without collapsing it, and essentially the same force will be applied each time, regardless of who the user is. These forces will be essentially the same because lever 16 pivots through the same arc each time it moves to its closed position and plunger 20 moves the same axial distance, this distance being further governed by shoulder 20X on plunger 20 as seen in FIG. 2 being stopped by shoulder 12X of body 12.

As noted earlier, the plug may have a variety of cross-sections and still achieve the same general functions. Thus, the plug may be circular as seen in FIG. 10, or may have flats as seen in FIG. 4, or may be hexagonal, octagonal, or may have other irregular shapes, so long as it deforms or compresses radially inward when axially compressed.

It has been found that forming flats on the outer surface of the plug established some areas or zones which have outer diameter conforming generally to the bore or inner diameter 24 of the connector body and intermittent areas or zones of the plug's outer surface which have smaller outer diameter. These latter areas will deform radially outward before the plug deforms radially inward against the catheter, because these outer areas are adjacent air space which poses no resistance. After this initial outward deformation, the plug is snugly confined and set in its position, and it will then deform radially inward, generally uniformly around the engaged length and outer circumference of the catheter. The plug's outer diameter may initially fit snugly within the bore or it may have clearance.

The plug illustrated in FIG. 4 has six uniformly spaced flats, each two adjacent flats being separated by a longitudinal zone of arcuate circular diameter that is the maximum diameter of the plug and corresponds to the bore diameter 24 of body 12. The diameter between any two opposite flats is the minimum diameter of the plug and is the area where the principal radial outward deformation of the plug will occur. The plug is preferably uniform in cross-section along its length; however, the cross-section may also vary along the length.

As seen in FIG. 6, the plunger 20 has a proximal end to apply axial force to most of the exposed end of plug 18, and has a distal end with a conical recess to easily receive the proximal end of the catheter 22 when inserted. Also, pivot body 16B has a divergent opening 16D as seen in FIGS. 1–2 and 4–6 to allow pivoting while the catheter extends therethrough.

Spring latching of lever 16 is achieved as follows. As seen in FIGS. 1–6 spring latch 14 is a generally cylindrical member having a longitudinal slot 40 at the top, a central recess 42 (see FIG. 3), a longitudinal tooth 44 extending radially inward on both sides (see FIGS. 3 and 4), and a longitudinal recess 46 extending outward on both sides (see FIGS. 3 and 4). This member 16 further includes spring fingers 48 which are deflectable axially to the left, which then urge latch member 14 to move to the left. As seen in FIGS. 4 and 5 pivot arm 16 has latch tabs 16L which cooperates with latch recesses 46 in latch 14 (seen in FIGS. 3 and 4) as follows.

The normal position latch 14 is to the left as seen in FIG. 1 due to the spring force applied to the left by latch spring fingers 48. This latch is manually movable to the right (distally) when a user grips the latch, preferably by the ribbed surface and slides it distally to the right. When the lever arm 16A is down in closed position of FIGS. 1–3 with the catheter constrained as described above, latch 14 is spring biased to the left where its outward recesses 46 have received and hold projections 16L of the lever arm and thus restrain this arm from pivoting clockwise back to its open position which would release the catheter. Manual sliding of the latch releases the lever arm, and the compressed plug then urges the lever to pivot to the open position. This quickly and automatically releases the catheter, this release being achieved by a simple finger or thumb action of a single hand of the user.

As seen in FIG. 3, the latch 14 remains coupled to the body 12 by the fact that its longitudinal teeth 44 overlie and slide against shoulder 26 of body 12. This latch is resiliently spread open to slide transversely onto body 12 until the teeth 44 snap onto shoulder 26. The latch is thus coupled onto the body 12 but free to be slid axially by the user.

As seen in FIG. 5, the distance of travel L1 of the latch 14 is greater than the length L2 of the lever arm projection 16L, so that axial motion of latch 14 will uncover and release the lever arm; however, until manual release of latch 14, the lever will remain safely locked.

FIGS. 8–12 illustrate a second embodiment of the catheter connector, generally similar to the first and which will bear identical reference numbers for all elements except those few where there are differences. The first difference is that the lever pivot pin and pivot pin recess are reversed. The first embodiment in FIG. 4 shows pin 16P on the lever 16, whereas the second embodiment has pivot pin 52 on body 12. Similarly, the first embodiment in FIG. 4 shows the pivot pin recess 34 on the body 12, whereas the second embodiment in FIG. 10 shows the pivot recess 50 on lever 16.

Figure 12:
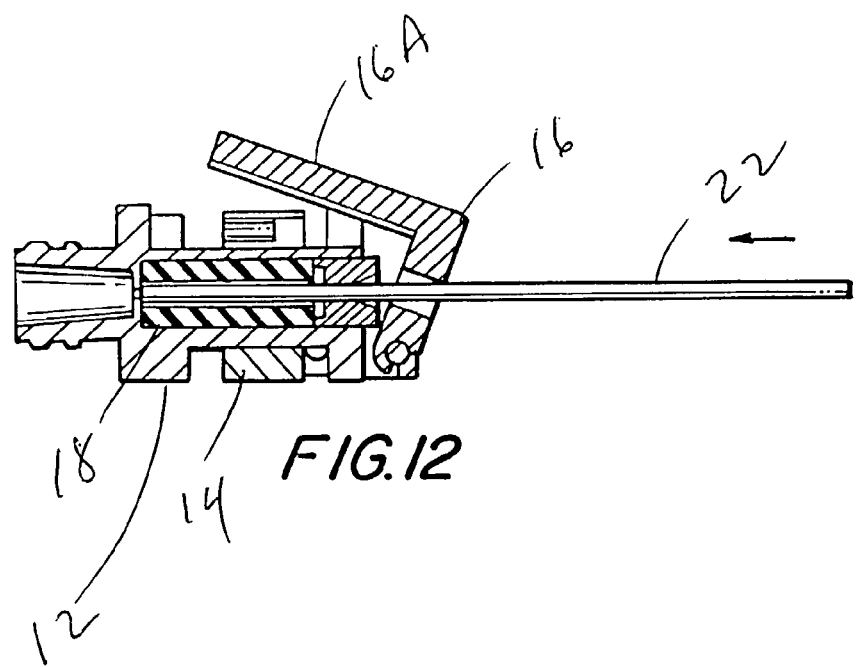
FIG. 12 is a longitudinal sectional view taken along line 12—12 in FIG. 11.

Next, the stop or shoulder 16S of FIG. 2 is not present in the second embodiment in FIG. 12. Also, the ledge or shoulder 26 of body 12 mating tooth 44 of latch 14 are not present in the second embodiment connector of FIG. 10.

The components of the new catheter connector are made by manufacturing methods long known in the relevant prior art and typically of injection molded plastic.

The invention maybe embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A catheter connector operable between a first condition of being coupled to one end of a catheter and a second condition of being uncoupled from said catheter, comprising:
   (a) a body part including therein a cylindrical bore having bore surface walls and a proximal end wall,
   (b) an elastically compressible tubular plug situated within said body part bore and having a proximal end adjacent said proximal wall of said body part and an opposite distal end, said plug having a bore, said plug having a first condition where its bore can receive said end of said catheter and a second condition where after it has received said end of said catheter and after it is axially compressed, it deforms radially inwardly and applies a radially inward force onto said catheter,
   (c) a lever mounted on said body part and pivotal between an open position which leaves said plug relaxed and a closed position applying axial force on said plug, whereby said plug being constrained by said bore surface walls and proximal end wall of said body part, is axially compressed and deforms radially inward against and tightly engages said end of said catheter when it is positioned therein, and
   (d) latch means that operates between locked and unlocked conditions, said latch means comprising first coupling means on said body part and second coupling means on said lever, said first coupling means being movable on said body part to releasably engage said second coupling means when said lever is in its closed position to thereby put said latch in its locked condition which maintains said lever in said closed position,
   said body part further comprising spring means which constantly and resiliently urges said first coupling means into its engaged condition with said second coupling means.

2. A catheter connector according to claim 1 wherein said spring means is an integral extension from said first coupling means.

3. A catheter connector according to claim 1 wherein said body part includes a first pivot element, and said lever includes a second pivot element, said first and second pivot elements being coupled together for said lever to pivot.

4. A catheter connector according to claim 3 wherein said first pivot element is a pin on said lever, and said second pivot element is a recess in said body part in which said pin is situated.

5. A catheter connector according to claim 3 wherein said first pivot element is a pin on said body part, and said second pivot element is a recess in said lever in which said pin is situated.

6. A catheter connector according to claim 1 wherein said plug in cross-section is a generally symmetrical polygon with a plurality of flats.

7. A catheter connector according to claim 6 wherein said polygon is an octagon.

8. A catheter connector according to claim 6 wherein and polygon is a hexagon.

9. A catheter connector according to claim 1 wherein said plug in cross-section is generally round, and whose outer surface has a plurality of circumferentially spaced-apart circumferential arcs and with a flat between each two adjacent arcs.

10. A catheter connector according to claim 6 wherein said plug in cross-section defines opposite flats and opposite points, and wherein each two adjacent flats intersect as a point, and opposite flats define a first diameter and opposite points define a second diameter larger than said first diameter.

11. A catheter connector according to claim 1 wherein said spring means comprises a finger which extends from said first coupling means and contacts said body part, always urging said first coupling means to remain engaged to said second coupling means and to thereby maintain said lever in its closed condition until said front coupling means is manually moved axially to release said lever to move to its open condition.

12. A catheter connector according to claim 1 wherein said plug comprises rubber.

13. A catheter connector according to claim 1 wherein said plug applies inward radial force on said proximal end of said catheter substantially equally around said circumference of said catheter.

14. A catheter connector according to claim 1 wherein said first coupling means slidably engages said body part for axial movement thereon, and said spring means has a proximal part joined to said first coupling means and a distal part engaging said body part and constantly urging said first coupling means toward its locked condition.

15. A catheter connector according to claim 13 wherein said first coupling means is a sleeve at least partially encompassing said body part and said first coupling means is a spring finger extending from said sleeve.

16. A catheter connector operable between a first condition of being coupled to one end of a catheter and a second condition of being uncoupled from said catheter, comprising:

(a) a body part including therein a cylindrical bore having bore surface walls and a proximal end wall, (b) an elastically compressible tubular plug situated within said body part bore and having a proximal end adjacent said proximal wall of said body part and an opposite distal end, said plug having a bore, said plug having a first condition where its bore can receive said end of said catheter and a second condition where after it has received said end of said catheter and after it is axially compressed, it deforms radially inwardly and applies a radially inward force onto said catheter, (c) a lever mounted on said body part and pivotal between an open position which leaves said plug relaxed and a closed position applying axial force on said plug, whereby said plug being constrained by said bore surface walls and proximal end wall of said body part, is axially compressed and deforms radially inward against and tightly engages said end of said catheter when it is positioned therein, and (d) latch means that operates between locked and unlocked conditions, said latch means comprising first coupling means on said body part and second coupling means on said lever, said first coupling means being movable on said body part to releasably engage said second coupling means when said lever is in its closed position to thereby put said latch in its locked condition which maintains said lever in said closed position, wherein said body part has a central longitudinal axis and said lever has a central longitudinal axis generally perpendicular to said body pares central longitudinal axis, and said second coupling means on said lever comprises a tab on each side extending transversely outward from said central longitudinal axis of said lever, and said first coupling means is slidable on said body and has a groove on each side into which one of said tabs is extendable.

17. A catheter connector operable between a first condition of being coupled to one end of a catheter and a second condition of being uncoupled from said catheter, comprising:

(a) a body part including therein a cylindrical bore having bore surface walls and a proximal end wall, (b) an elastically compressible tubular plug situated within said body part bore and having a proximal end adjacent said proximal wall of said body part and an opposite distal end, said plug having a bore, said plug having a first condition where its bore can receive said end of said catheter and a second condition where after it has received said end of said catheter and after it is axially compressed, it deforms radially inwardly and applies a radially inward force onto said catheter, (c) a lever mounted on said body part and pivotal between an open position which leaves said plug relaxed and a closed position applying axial force on said plug, whereby said plug being constrained by said bore surface walls and proximal end wall of said body part, is axially compressed and deforms radially inward against and tightly engages said end of said catheter when it is positioned therein, and (d) latch means that operates between locked and unlocked conditions, said latch means comprising first coupling means on said body part and second coupling means on said lever, said first coupling means being axially slidable on said body part to releasably engage said second coupling means when said lever is in its closed position to thereby put said latch in its locked condition which maintains said lever in said closed position, wherein said body part has a pair of outward and axially extending shoulders, and said first coupling means has a pair of inward extending tabs adapted to engage said shoulders for restraining said first coupling mean from disengagement with said body part while allowing axial slidable movement thereon.

18. A catheter connector operable between a first condition of being coupled to one end of a catheter and a second condition of being uncoupled from said catheter, comprising:

(a) a body part including therein a cylindrical bore having bore surface walls and a proximal end wall,
(b) an elastically compressible tubular plug situated within said body part bore and having a proximal end adjacent said proximal wall of said body part and an opposite distal end, said plug having a bore said plug having a first condition where its bore can receive said end of said catheter and a second condition where after it has received said end of said catheter and after it is axially compressed, it deforms radially inwardly and applies a radially inward force onto said catheter,
(c) a lever mounted on said body part and pivotal between open and closed positions, said lever when pivoted from open to closed position applying axial force on said plug, which plug being constrained by said bore surface walls and proximal end wall of said body part, is axially compressed and deforms radially inward against and tightly engages said end of said catheter when it is positioned therein, and
(d) latch means that operates between: (i) a locked condition where it maintains said lever in its closed position, and (ii) an unlocked condition where it releases said lever to move to its open position, wherein said lever when released by said latch means is urged by said compressed plug to move to its open position.

19. A catheter connector operable between a first condition of being coupled to one end of a catheter and a second condition of being uncoupled from said catheter, comprising:
(a) a body part including therein a cylindrical bore having bore surface walls and a proximal end wall,
(b) an elastically compressible tubular plug situated within said body part bore and having a proximal end adjacent said proximal wall of said body part and an opposite distal end, said plug having a bore, said plug having a first condition where its bore can receive said end of said catheter and a second condition where after it has received said end of said catheter and after it is axially compressed, it deforms radially inwardly and applies a radially inward force onto said catheter,
(c) a lever mounted on said body part and pivotal between open and closed positions, said lever when pivoted from open to closed position applying axial force on said plug, which plug being constrained by said bore surface walls and proximal end wall of said body part, is axially compressed and deforms radially inward against and tightly engages said end of said catheter,
(d) latch means that operates between locked and unlocked conditions, said latch means comprising
    i. first coupling means formed a sleeve at least partially encompassing said body part and axially slidable thereon,
    ii. second coupling means on said lever, said sleeve being slidable from a first position where said latch is unlocked to a second position where said second coupling means releasably engages said first coupling means, whereby said latch will be in its locked condition which maintains said lever in its closed condition, and
    iii. spring means engaging said sleeve and said body part and constantly urging said sleeve to its second position,
said sleeve being manually slidable by an operator back to its first position, thus unlocking said latch which allows said lever to move to its open condition.

* * * * *